United States Patent [19]
Fridley et al.

[11] 4,061,020
[45] Dec. 6, 1977

[54] DEFORMETER

[75] Inventors: Robert B. Fridley; Pictiaw Chen; James J. Mehlschau; Lawrence L. Claypool, all of Davis, Calif.

[73] Assignee: The Regents of the University of California, Berkeley, Calif.

[21] Appl. No.: 714,184

[22] Filed: Aug. 13, 1976

[51] Int. Cl.² .............................................. G01N 3/48
[52] U.S. Cl. ............................................ 73/81; 73/83
[58] Field of Search ...................... 73/81, 83; 198/340, 198/341, 502

[56] References Cited

U.S. PATENT DOCUMENTS

| | | | |
|---|---|---|---|
| 2,520,387 | 8/1950 | Dobry et al. ............................. | 73/81 |
| 3,901,381 | 8/1975 | Quinn ...................................... | 198/341 |

FOREIGN PATENT DOCUMENTS

| | | | |
|---|---|---|---|
| 2,249,325 | 4/1973 | Germany ................................. | 73/81 |

Primary Examiner—Richard C. Queisser
Assistant Examiner—Anthony V. Ciarlante
Attorney, Agent, or Firm—Lothrop & West

[57] ABSTRACT

A deformeter for testing the firmness of fruit as an indication of its maturity includes a support for an individual fruit effective to convey the fruit to a testing location, at which sensors are urged to contact the fruit surface lightly, preferably on a diameter, to establish a datum position. The sensors are then urged to contact the fruit with a predetermined, deforming pressure. At least one more sensor moves correspondingly into the fruit to establish an indented position. The two sensor positions are electrically noted and are subtracted to afford an indented distance from datum position indicative of firmness and so maturity. A modification uses a pair of first sensors arranged on opposite sides of the fruit in a trailing position, the pairs operating in sequence and being arranged with all sensors substantially in the same, vertically adjustable plane.

17 Claims, 9 Drawing Figures

DEFORMETER

BRIEF SUMMARY OF THE INVENTION

Fruit advancing intermittently or steadily in a path to a station is lightly contacted at the station to establish a datum location of the fruit surface and then is more heavily contacted at the station with a predetermined force to produce an indentation, the amount of which is measured from the datum location and is indicative of firmness and maturity.

DETAILED DESCRIPTION

Figure 1:
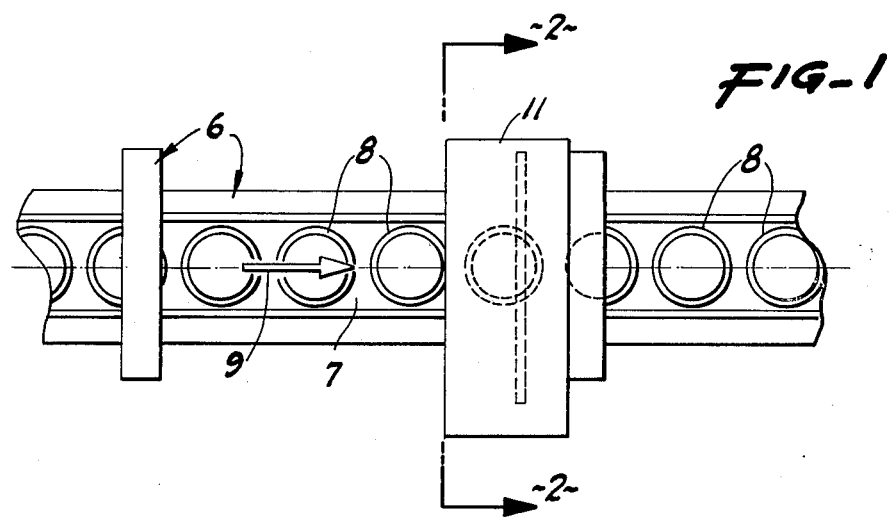
FIG. 1 is a plan view, portions being broken away, of one embodiment of a deformeter constructed pursuant to the invention, housings being in place.
Figure 3:
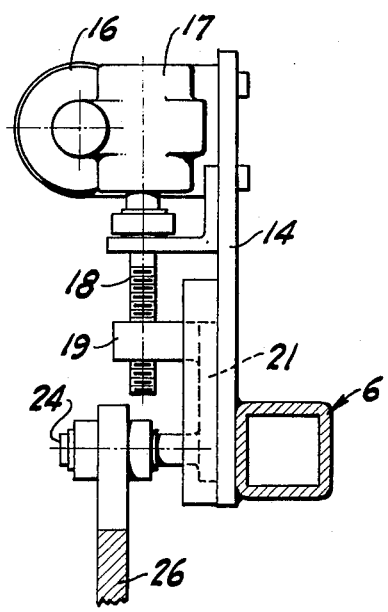
FIG. 3 is a cross-section of an elevator in detail, the plane of which is indicated by the line 3—3 of FIG. 2.
Figure 4:
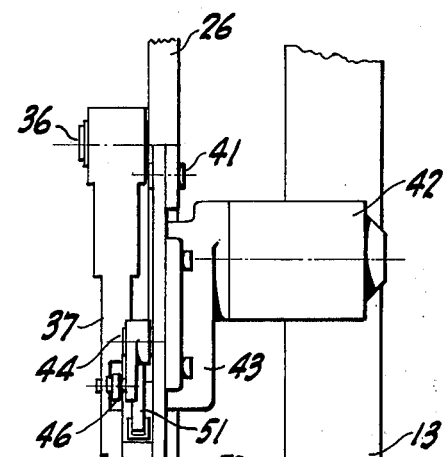
FIG. 4 is a partial side elevation taken as indicated by the line 4—4 of FIG. 2.
Figure 4:
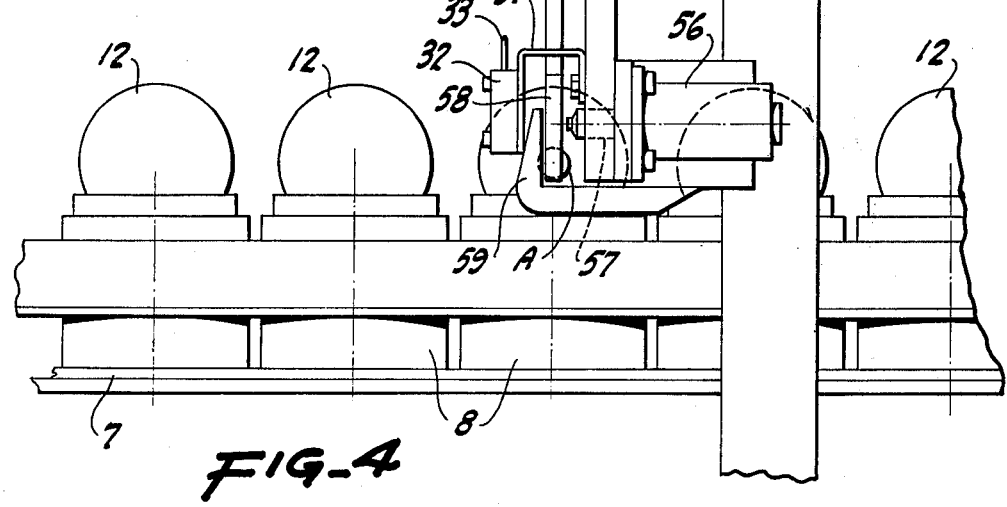

Various fruits must be rather carefully handled for storage or marketing, or both, in order to maximize the return to the producer. Many fruits can be sent to storage or directly to market, depending largely on their maturity when the choice of routing must be determined. Various fruits do not afford a good external, visual indication of maturity. Destructive testing of samples is sometimes resorted to. This is not economically advantageous, so investigations have been made to determine whether or not there is a workable relationship between the firmness of the fruit and its maturity. Such investigations have afforded a good correlation between firmness and maturity, at least for present purposes. A fair test for firmness is to subject the fruit to a predetermined or selected, standard pressure and then measure the amount of deformation or indentation produced, always short of disrupting the skin or damaging the cells of the fruit. The distance of depth of the deformation is utilized as an index of maturity. This test has been found to work very well with commercial varieties of pears and with other, similar fruits. Performed individually and manually, the test, although accurate, is time consuming. We have therefore developed machines, which we call deformeters, for testing individual fruits either in a relatively deliberate fashion allowing time for some auxiliary observations or in a relatively rapid fashion not delayed for auxiliary inspection but at a rate conducive to economical handling of large fruit quantities and permitting testing of each fruit individually.

In the first form of our deformeter, as illustrated in FIGS. 1-4, there is provided a frame 6 having a conveyor 7 thereon incorporating a number of upstanding, individual, generally circular cylindrical cups 8. The cups are advanced step by step in the direction of the arrow 9 in FIG. 1 toward a testing station represented by an enclosure 11 or housing for the protection of the mechanism. In the other figures, the housing is removed for clearer illustration. An individual fruit such as a pear 12 is positioned by hand in one of the cups 8. Manual closure of a starting switch (not shown) causes motor advancement of the loaded cup on the frame toward an upright 13 constituting an arch, FIG. 2. A base plate 14 upstanding from the arch carries an electric motor 16 having a reduction gear 17 through which a screw shaft 18 is driven. A nut 19 in engagement with the screw shaft is on an elevator slide 21 guided in ways 22 and 23 upstanding from the plate 14.

Means are provided for initially centering the mechanism on the fruit. The slide 21 at its lower end carries a longitudinally extending pivot pin 24 acting as a fulcrum for a main pendulum 26 hanging freely from the pin. The main pendulum includes a plate of somewhat irregular but generally triangular configuration serving to carry a number of instrumentalities. When fully equipped and loaded, the main pendulum hangs with its center line 27 approximately corresponding with the center line of each of the cups 8 on the conveyor. The individual fruits, although somewhat irregular in practice, generally are of approximately geometrical forms and are illustrated herein as having spherical portions. A pear 12 is illustrated stem end down and in a position entirely symmetrical with the center line 27, although this is only rarely the case. Sensors A and B are carried by the main pendulum and are used, as later described, in an individual centering operation. The height of an individual fruit or the distance it extends above an individual cup 8 likewise varies. To compensate for this variation, a bracket 31 secured to the main pendulum 26 supports a double electrical switch 32 and also a hinged feeler finger 33 extending across the center line of the machine.

To start machine operation, the main starting switch (not shown), is manually closed. This closure, among other things, energizes the motor 16 to raise the main pendulum 26 to its uppermost position, as controlled by a standard limit switch (not shown). If such pendulum is already raised, the motor 16 is not energized. The starting switch closes a relay logic circuit controlling a single cycle mechanism advancing the conveyor 7 one intermittent step to position the next individual cup within the housing 11 at the gauging station. After sufficient time for this to occur, the relay logic starts the motor 16 in a reverse direction and lowers the main pendulum until the finger 33 engages the individual fruit in the stationed cup. Whatever the height of the flower end of the fruit, contact therewith causes the lowering finger 33 to open the switch 32 to stop the motor 16. The main pendulum is thus lowered and held at a height with respect to the top or flower end of the fruit and approximately to establish the level of the sensors A and B in a horizontal plane at about the maximum diameter of the fruit.

The height setting or adjustment is followed by a centralizing or centering operation. For this reason, there is mounted on a pin 36 on the main pendulum 26 an auxiliary pendulum 37 depending by gravity and at its lower end carrying the sensor A. This is in the form, preferably, of a ball 38 fixed in place on the auxiliary pendulum.

Additionally mounted on the main pendulum 26 is a tertiary pendulum 39 depending from a mounting pin 41 and hanging by gravity. On the tertiary pendulum is a zeroing motor 42 having a gear motor 43 to a crank arm 44 connected by a pitman 46 to the auxiliary pendulum 37. Before the centering operation and before the motor 42 is energized, the parts hang by gravity with the sensors A and B separated far enough to be slightly away from a fruit of the maximum expected size. The sensor B is releasably fixed to the main pendulum 26, as will later be described.

Figure 2:
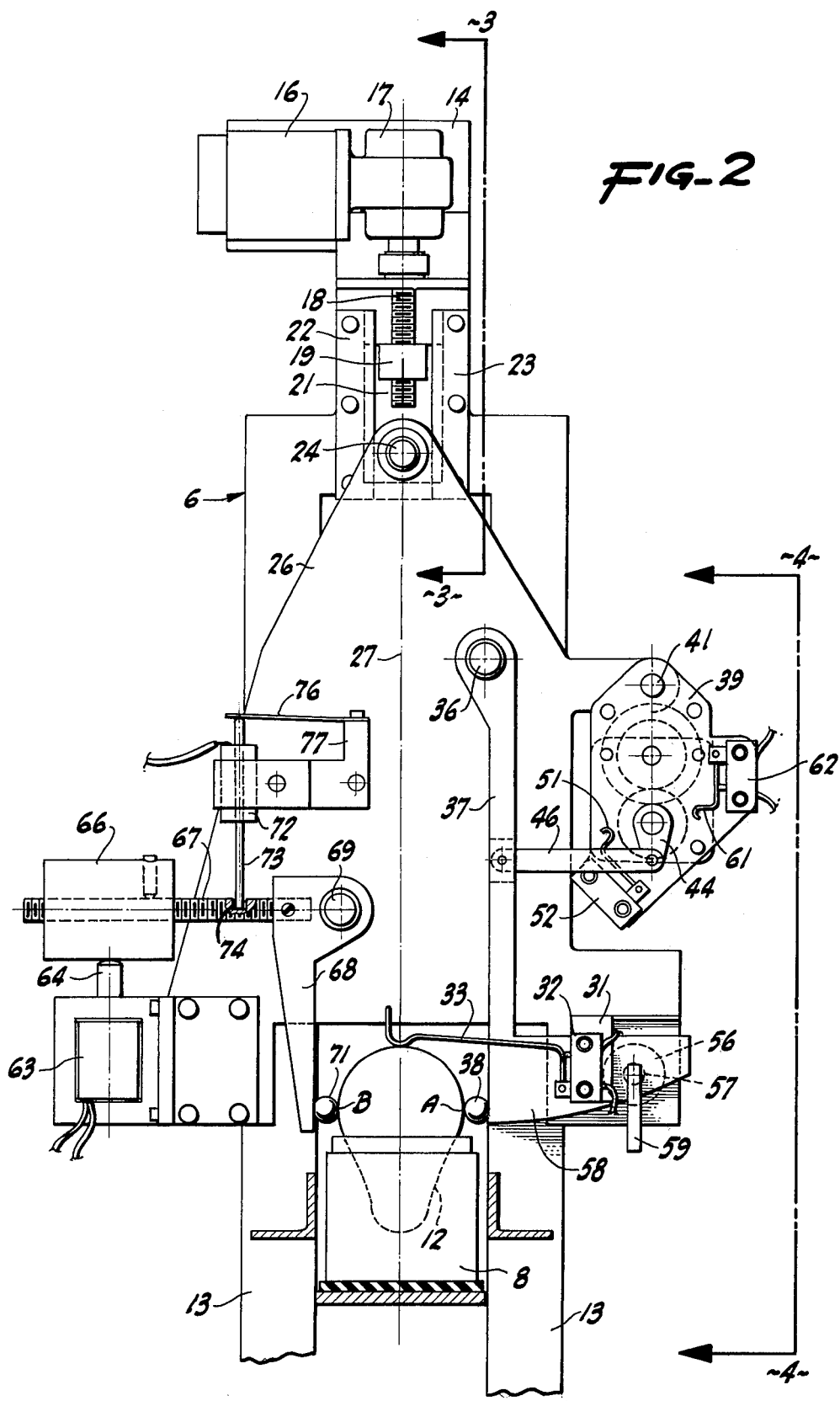
FIG. 2 is a cross-section, the plane of which is indicated by the line 2—2 of FIG. 1.

The crank arm 44 can be considered to start from a rest position at 90 degrees from the position shown in FIG. 2 and with the crank arm 44 at three o'clock. Actuation of the dual switch 32 by lowering of the main pendulum energizes a logic relay to start the motor 42 to rotate the crank 44 in a clockwise direction toward the position seen in FIG. 2. As this occurs, the pitman 46 swings the auxiliary pendulum 37 in a clockwise direction or generally toward the left in FIG. 2 toward and through the position shown in that figure.

The force that can be imposed on the fruit is limited. As soon as the sensor A contacts the fruit, the reaction force acting through the pin 36 rotates the main pendulum 26 slightly counterclockwise until the sensor B also abuts the surface of the fruit. The sensors A and B contact the fruit definitely but quite lightly, only enough for centering or establishing a datum and not nearly enough to produce any indentation. This contacting force may be further limited. The tertiary pendulum 39 may also swing as the sensors A and B lightly contact the surface of the fruit 12.

The points of contact are and remain substantially at the maximum horizontal diameter of the fruit, as determined by the previous height adjustment. This is not a mathematically exact relationship, but is within reasonable practical limits. The machine thus can be utilized with successive fruit of varying, different sizes and obviates the necessity of sizing the fruit before checking.

The motor 42 continues its operation until the crank arm 44 in about an eight o'clock position comes into contact with a switch arm 51 on a dual switch 52 mounted on the tertiary pendulum 39. Operation of the switch 52 stops the motor 42 and starts a relay delay period, allowing the parts to stabilize, and also actuates a pendulum holding mechanism. Mounted on the main pendulum 26 (FIG. 4) is a solenoid 56 having a plunger 57 arranged on one side of a blade extension 58 or "hatchet" of the auxiliary pendulum 37. The extension, when free, moves or swings between the end of the plunger 57 and a backstop hook 59 also secured to the main pendulum 26.

When the dual switch 52 actuates its relay, the solenoid 56 is energized to project the plunger 57 to abut the extension 58 and deflect it slightly to bear against the hook 59. Thus, the extension 58 in its momentary position set by fruit sensing is clamped tightly between the solenoid plunger and the hook 59. The instantaneous position of the sensors A and B is thus fixed with respect to the main pendulum 26, centered upon the fruit of whatever size. The parts are held in such position with a constant, minimum surface pressure during a short, ensuing stabilizing delay. A delay relay in the electrical circuit keeps the solenoid 56 energized for a predetermined time.

When the crank arm 44 is in abutment with the switch arm 51, the delay circuit controlled by the dual switch 52 opens a circuit to a solenoid 63 mounted on the main pendulum plate 26. This circuit was energized by the initial closure of the main switch. The solenoid is part of the mechanism for the sensor B. The solenoid 63 has a plunger 64 which, in the ordinary, energized condition of the solenoid, serves as a releasable support for a load weight 66. For adjustment the weight is mounted on one threaded arm 67 of a bell crank lever 68 swingably mounted on a pin 69 on the main pendulum 26. The lower end of the other arm of the bell crank 68 carries the sensor B. This has the form of a ball 71 disposed in the same general plane as the sensor ball 38.

Initially the ball 71 is barely in contact with the surface of the fruit, but after a relay delay following operation of the dual switch 52, the solenoid is deenergized and allows the plunger 64 to fail. This abruptly removes the support from the weight 66. The bell crank 68 and the sensor B are no longer held with respect to the main pendulum 26. As the weight 66 falls freely, the bell crank lever 68 rotates in a counterclockwise direction (FIG. 2) and drives the sensor ball 71 with a predetermined, standard force into the material of the fruit. The distance of ball penetration is related to the firmness of the fruit. The relative position of the sensors A and B then changes from the previous datum position to a new relative position with respect to the fruit. Since the position depends upon the fruit's firmness, and firmness is related in a known way to maturity, the new position also indicates maturity.

Motion of the bell crank lever 68 is sensed by an electrical detector 72. This is actuated by a through rod 73 lodged in a depression 74 in the screw arm 67 and urged lightly thereagainst by a leaf spring 76 mounted on a bracket 77 on the main pendulum plate 26 which also holds the detector 72. Initially the detector gives an electrical reading of the starting or datum position. Then, after rotation of the bell crank, the new rod position is reflected by a reading of the amount of deformation of the fruit under the standard force of the released weight 66. The change in condition of the sensors from initial, bare contact position to final, indented position is measured by the detector 72 and affords an indication of the fruit maturity.

Shortly after the solenoid 63 is deenergized; say, about one second thereafter, the delay circuit responsive to the switch 52 allows the solenoid 56 to deenergize and free the blade extension 58 and also restores energization to the motor 42 to advance the crank 44 from eight o'clock position to three o'clock position adjacent a switch arm 61. A switch 62 on the pendulum 39 is operated by the switch arm 61 in the three o'clock position of the crank 44. This stops the rotation of the motor 42 and leaves the crank in this location. Operation of the switch 62 also reenergizes the solenoid 63 to lift the load weight 66, and additionally energizes the motor 16 to lift the elevator slide 21 to its original, top position. The limit switch (not shown) stops the slide 21 at the top. The whole operation, having come full cycle, can be repeated manually or automatically by the top limit switch with a subsequent fruit.

The foregoing mechanism is effective to derive the firmness of the fruit by an indentation test and operates individually on the fruit in a relatively deliberate manner so that the fruit can also be visually inspected for other factors. While this operation is quite thorough, it nevertheless is not fast enough for quantity testing in packinghouse use, for example. We therefore have provided a variation in the form of a device as shown in FIGS. 5-9 inclusive.

Figure 5:
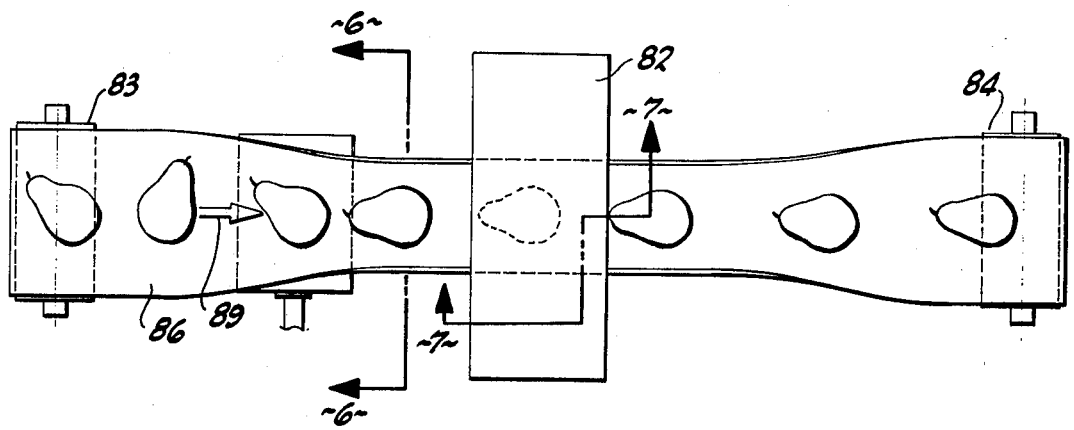
FIG. 5 is a plan of a modified form of deformeter with a housing in place, certain portions being illustrated diagrammatically.
Figure 6:
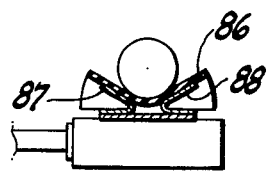
FIG. 6 is a cross-section, the plane of which is indicated by the line 6—6 of FIG. 5.
Figure 9:
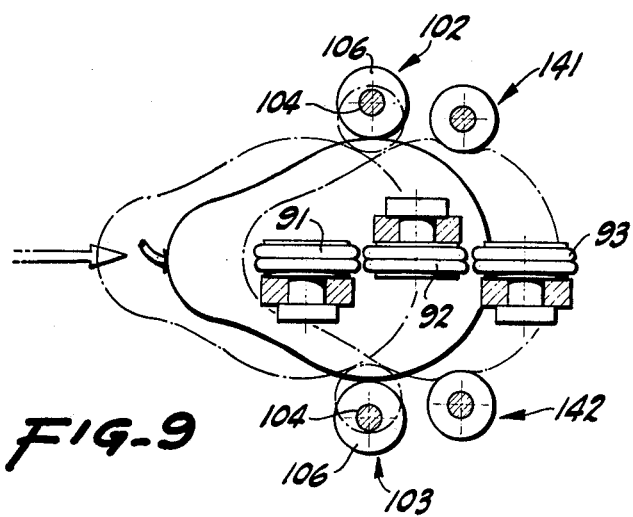
FIG. 9 is a cross-section, the plane of which is indicated by the line 9—9 of FIG. 7, portions of the surrounding mechanism being omitted for clarity.
Figure 7:
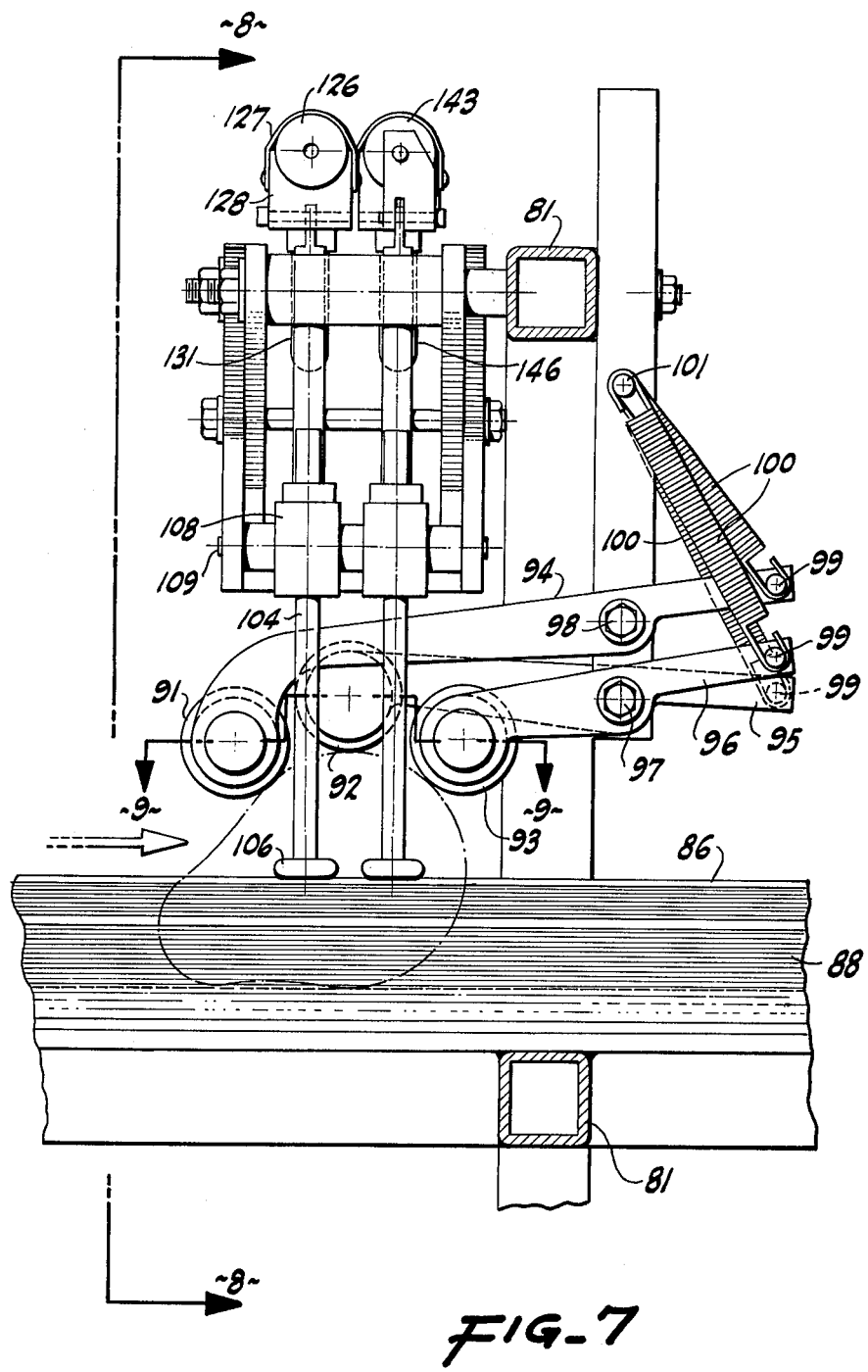
FIG. 7 is a cross-section, the planes of which are indicated by the line 7—7 of FIG. 5.
Figure 8:
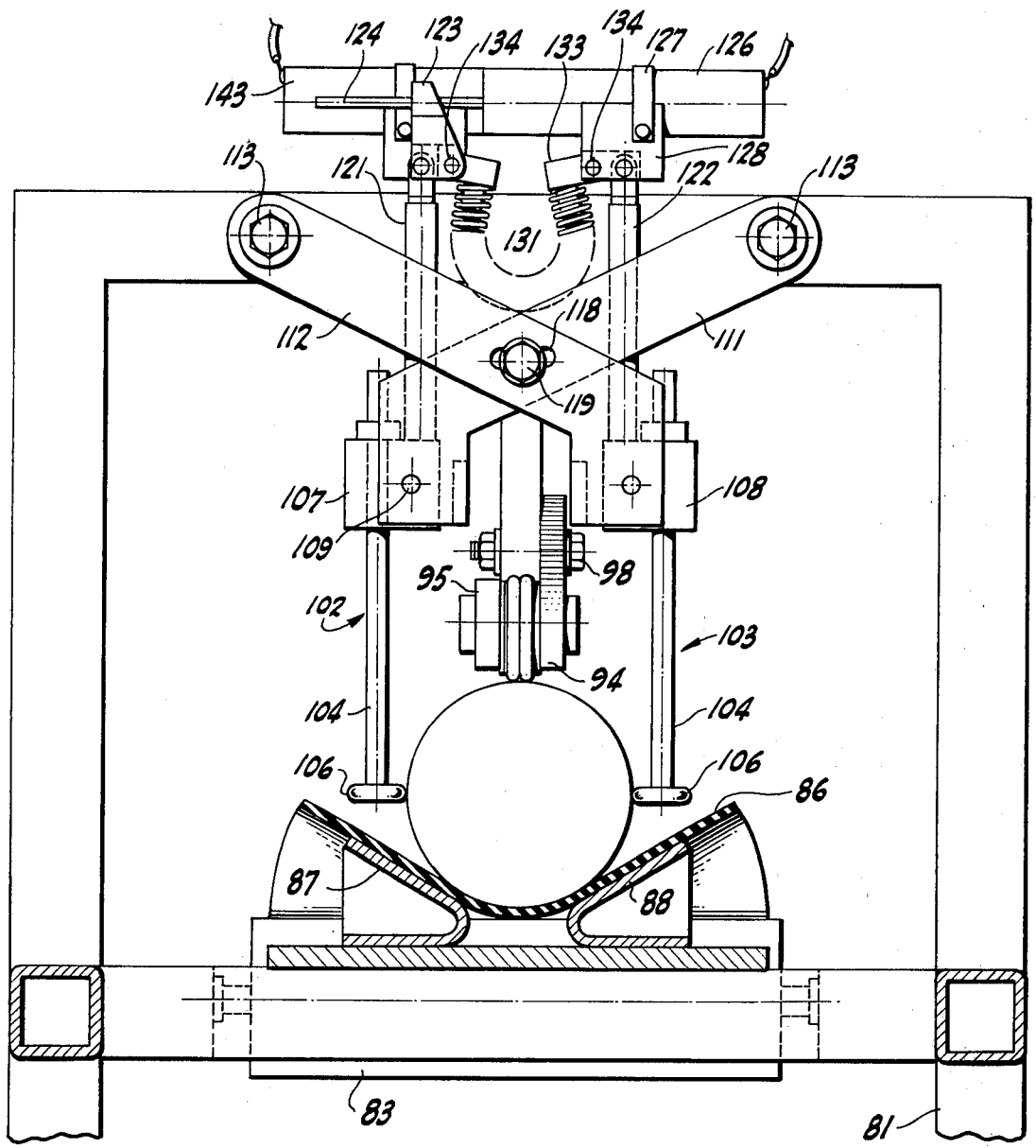
FIG. 8 is a cross-section, the plane of which is indicated by the line 8—8 of FIG. 7.

In this arrangement, there is a frame 81 (FIG. 7) inclusive of a housing 82 (FIG. 5) at the gauging station. On the frame and mounted on suitable rollers 83 and 84 thereon is a conveyor belt 86. Around the rollers and in its lower run the belt is relatively flat, but between its ends the upper run of the belt is troughed by contact with deflecting plates 87 and 88 arranged so that the central portion of the conveyor belt, which travels in the direction of the arrow 89 in FIG. 5, is made upwardly concave or like a trough. The effect is that when a fruit, such as a pear, is positioned on the initial, relatively flat portion of the conveyor belt and is carried along, the fruit in entering the troughed portion of the belt tends to align with its longitudinal or stem-flower axis coinciding with the longitudinal, central axis of the machine. A vibrator on the under side of the belt may assist in fruit orientation. It is immaterial whether the fruit, such as a pear, illustrated, enters the troughing portion of the belt stem end first or flower end first. In any case, the pear is longitudinally arrayed and is generally centralized.

As the pear advances on the belt, it is pressed downwardly against the belt with considerable firmness so that the pear tends not to slip on the belt. The fruit is frictionally loaded and travels along at or very close to the speed of the belt. Downward pressure is accomplished by providing on the frame 81 an endless chain or belt, not shown, or, as shown, a series, in this case, three, of aligned friction rollers 91, 92 and 93 at the gauging station. Each of the rollers is mounted for rotation on its respective one of a plurality of arms 94, 95 and 96. The arms, in turn, are pivotally mounted on the frame 81 by pivot bolts 97 and 98. The levers are extended and carry attachment pins 99 for coil springs 100 likewise hooked on a pin 101 on the frame 81. All of the rollers are thus urged toward the belt with a predetermined spring force, so that the pear or other fruit must necessarily follow along with the conveyor.

Within the station there is provided a pair of leading sensors 102 and 103. These are substantially symmetrical with respect to the center line of the machine. Each sensor includes a rod 104 having a rotatable sensor wheel 106 at the lower end thereof. The rods 104 go through blocks 107 and 108, respectively. The blocks 107 and 108 are pivotally mounted by pins 109 in the lower end of link levers 111 and 112. At the upper, fulcrum end the levers are connected by pivot bolts 113 to the frame 81. The levers 112 are provided with elongated openings 118 through which a central adjusting bolt 119 extends. When the bolt 119 is loose, the levers 112 can easily be moved up and down into any position and are held there by a tightened bolt 119. The sensor wheels 106 are always coplanar and can be set at any desired height, preferably corresponding to the maximum diameter of the fruit on the belt. Since this adjustment is usually set in advance of any predetermined run, it is advisable first to size the fruit to be tested and to feed fruit all of one size in one run, so that the sensor wheels 106 engage the fruit substantially on a large diameter thereof. This is easy to do since in most packing and handling establishments sizing is a standard operation.

The blocks 107 and 108 respectively carry upright arms 121 and 122. The arm 121 at its upper end carries a bracket 123 firmly secured thereto. The bracket is also firmly in engagement with a moving, sensing member 124, such as a rod, entering into and movable transversely with respect to a mating, movable electrical sensing member having a case 126. A clamp 127 and a bracket 128 firmly secure the electrical member 126 to and at the upper end of the arm 122.

Means are provided for urging the electrical sensors 124 and 126 and their corresponding arms 121 and 122 and the leading sensor wheels 106 into a fruit-engaging position. This is done by means of a relatively light or relatively weak coil spring 131 formed into a generally U shape and connected by end fittings 132 and 133 to the brackets 123 and 128 by pins 134. Thus, the leading sensor wheels 106 are urged toward each other. When a fruit on the conveyor advances between them, the sensor wheels ride over the surface of the fruit with very light, barely contacting pressure, shown by full lines in FIG. 9. The rod member 124 and the case 126 of the electrical measuring device are moved accordingly to arrive at a datum indication of the location of the fruit surface. Although the fruit is approximately centered by the troughing conveyor, it is not essential that the fruit be exactly centered, since the sensor wheels and the electrical mechanism follow in unison to one side or the other, according to the position of the fruit. The datum diameter is noted simply by the relative position of the rod 124 and the case 126. This affords an electrical datum indication of the position of the leading sensor wheels by light pressure only.

The leading pair of sensors 102 and 103 is almost exactly duplicated (FIG. 9) by a trailing pair of sensors 141 and 142 mounted just behind the leading sensors. The same mechanism is duplicated for the trailing sensors and locates them in substantially the same horizontal plane with the leading sensors. An electrical detector mechanism 143 is substantially identical with the detector members 124 and 126. The difference is that the trailing sensor mechanism is especially provided with a relatively strong spring 146 otherwise comparable to the weak spring 131.

After the datum reading has been taken, the travelling fruit comes into contact with and spreads the sensors 141 and 142 against a relatively strong but predetermined transverse pressure. The pressure is sufficient so that the sensors 141 and 142 move into the fruit a small amount, an amount dependent in a known way upon the firmness thereof. This movement is not sufficient to break the fruit skin or destroy any of the interior cells, but is effective upon the electrical sensor 143 to afford an indentation reading. The datum reading is electrically subtracted from this indentation reading to afford a net reading indicative of the depth or position of the sensor indentation and so the firmness and maturity of the fruit. With this arrangement the fruit travels substantially continuously through the machine, and the maturity readings are given in rapid succession as the individual fruits pass through the measuring station.

We claim:

1. A deformeter for testing the maturity of fruit comprising a frame, means for supporting a fruit on said frame, means on said movable into contact with said fruit, means for pressing said movable means into contact with said fruit to establish a datum position, means for limiting the pressure exerted on said fruit by said movable means, means for disabling said limiting means and for pressing said movable means into contact with said fruit under a predetermined load to establish an indented position, and means for detecting the difference between said datum position and said indented position.

2. A deformeter as in claim 1 in which said means movable into contact with said fruit includes a main pendulum, means for mounting said main pendulum on said frame, an auxiliary pendulum, means for mounting said auxiliary pendulum for swinging movement on said main pendulum, and means interconnecting said main pendulum and said auxiliary pendulum for urging said auxiliary pendulum into contact with said fruit with a force reacting upon and displacing said main pendulum.

3. A deformeter as in claim 2 in which said force is predetermined.

4. A deformeter as in claim 2 in which said means movable into contact with said fruit also includes a lever, means for mounting said lever on said main pendulum for movement toward and away from said fruit, means for urging said lever toward said fruit with a predetermined force, and means on said main pendulum for measuring said movement of said lever.

5. A deformeter as in claim 4 in which said measuring means is an electrical gauging device.

6. A deformeter as in claim 4 in which said lever urging means is a weight on said lever and disposed to fall from an upper position, and means for releasably holding said weight in said upper position.

7. A deformeter as in claim 6 in which said holding means is a solenoid.

8. A deformeter as in claim 4 in which said auxiliary pendulum and said lever are disposed to contact said fruit on opposite sides of said fruit.

9. A deformeter as in claim 2 including means for locking said auxiliary pendulum against swinging movement on said main pendulum.

10. A deformeter as in claim 9 in which said locking means is effective in any position of said auxiliary pendulum.

11. A deformeter as in claim 2 including a tertiary pendulum, means for mounting said tertiary pendulum for swinging movement on said main pendulum, a drive means mounted on said tertiary pendulum, and means for connecting said drive means to swing said auxiliary pendulum.

12. A deformeter as in claim 1 in which said means for supporting fruit on said frame includes a conveyor advancing said fruit through a leading station and a trailing station on said frame and in which said means movable into contact with said fruit includes a first pair of sensors movable toward and away from each other at said leading station and a second pair of sensors movable toward and away from each other at said trailing station.

13. A deformeter as in claim 12 in which a light spring urges said first pair of sensors toward each other and into said datum position in contact with said fruit and a heavy spring urges said second pair of sensors toward each other and into said indented position in contact with said fruit.

14. A deformeter as in claim 12 including means for urging a fruit on said conveyor into frictional driving engagement therewith.

15. A deformeter as in claim 12 in which said sensors include wheels.

16. A deformeter as in claim 12 in which said means movable into contact with said fruit is arranged with said pairs of sensors substantially in the same plane.

17. A deformeter as in claim 16 including means for adjusting said plane vertically with respect to said conveyor.

* * * * *